United States Patent [19]

Matsuzaki et al.

[11] Patent Number: 5,292,916
[45] Date of Patent: * Mar. 8, 1994

[54] METHOD OF PRODUCING CARBONIC ACID DIESTER

[75] Inventors: Tokuo Matsuzaki; Tuneo Shimamura; Satoru Fujitsu; Yoshinobu Toriyahara, all of Ube, Japan

[73] Assignee: Ube Industries, Ltd., Yamaguchi, Japan

[*] Notice: The portion of the term of this patent subsequent to Nov. 10, 2009 has been disclaimed.

[21] Appl. No.: 859,294

[22] PCT Filed: Sep. 30, 1991

[86] PCT No.: PCT/JP91/01313

§ 371 Date: May 22, 1992

§ 102(e) Date: May 22, 1992

[87] PCT Pub. No.: WO92/06066

PCT Pub. Date: Apr. 16, 1992

[30] Foreign Application Priority Data

Sep. 28, 1990 [JP] Japan .................... 2-257042
Sep. 28, 1990 [JP] Japan .................... 2-257043

[51] Int. Cl.$^5$ ............................... C07C 69/96
[52] U.S. Cl. ............................ 558/275; 558/260; 558/277
[58] Field of Search .................. 558/260, 275, 277

[56] References Cited

U.S. PATENT DOCUMENTS 5,162,563 11/1992 Nishihira .................... 558/260

FOREIGN PATENT DOCUMENTS

425197A3 5/1991 European Pat. Off. .
464460A3 1/1992 European Pat. Off. .
60-181051 9/1985 Japan .

Primary Examiner—Mary C. Lee
Assistant Examiner—Michael G. Ambrose
Attorney, Agent, or Firm—Finnegan, Henderson, Farabow, Garrett & Dunner

[57] ABSTRACT

A carbonic acid diester is stably and safely produced at a high selectivity and at a high yield by catalytically reacting carbon monoxide with a nitrous acid ester in a gas phase in the presence of a solid catalyst comprising a catalytic solid material carried on a solid carrier and comprising:

(a) a platinum group metal and/or a compound thereof,
(b) a compound of Fe, Cu, Bi, Co, Ni and/or Sn, and
(c) a vanadium compound, molybdenum compound, tungsten compound, sulfuric acid and/or phosphoric acid.

18 Claims, No Drawings

METHOD OF PRODUCING CARBONIC ACID DIESTER

DESCRIPTION

1. Technical Field

The present invention relates to a method of producing a carbonic acid diester.

More particularly, the present invention relates to a process of producing a carbonic acid diester selectively and stably from carbon monoxide and a nitrous acid ester.

the carbonic acid diester is very useful as a starting material of medicines and pesticides, and as an intermediate compound of a polycarbonate and urethane.

2. Background Art

A conventional method of producing a carbonic acid diester by a reaction of phosgene with an alcohol has been practiced for a long time. Nevertheless, this conventional method is disadvantageous in that phosgene has an extremely strong toxicity, and the reaction of phosgene with an alcohol produces hydrochloric acid as a by-product, which corrodes the reaction device. Therefore, there is a strong demand for a new method of producing a carbonic acid diester without using phosgene.

In response to this demand, various attempts have been made to produce a carbonic acid diester from an alcohol and carbon monoxide, (as disclosed in, for example, Japanese Unexamined Patent Publication (JP-A) No. 60-75,447, 63-72,650, and 63-38,010, and PCT-Publication No. WO-87/7601). In those methods, the carbonic acid diester is produced by a catalytic oxygen-oxidizing reaction of carbon monoxide with an alcohol in a liquid phase, in the presence of a catalyst consisting of a copper halide or palladium halide. These methods are disadvantageous in that, in the catalytic oxygen-oxidizing reaction, carbon dioxide is produced as a by-product, and thus the production of the carbonic acid diester is effected with a low selectivity based on the amount of carbon monoxide supplied to the reaction system. Also, the catalytic oxygen-oxidizing reaction produces water ($H_2O$) as another by-product, and thus the resultant carbonic acid diester must be isolated from the water by a refining procedure. Also, the above-mentioned methods are further disadvantageous in that the aimed carbonic acid diester must be separated from the catalyst in the reaction system. Accordingly, the above-mentioned methods are not satisfactory for industrial use.

Attempts have been made to eliminate the above-mentioned disadvantages, and as one such attempt, JA-A-60-181,051 discloses a method of producing carbonic acid diester by a catalytic oxidizing reaction of a nitrous acid ester with carbon monoxide, in a gas phase, in the presence of a catalyst composed of a solid platinum group metal or compound thereof carried on a solid carrier and an oxidant in an amount of 10 molar % in terms of $O_2$, per mole of carbon monoxide present in the reaction mixture.

In this method, however, although an oxidant, for example, oxgen, is added in the above-mentioned specific amount to the carbon monoxide, to inhibit a production of oxalic acid diester as a by-product, a certain amount of a by-product consisting of an oxalic acid diester is undesirably produced, and therefore, the selectivity of the aimed carbonic acid diester is low and the reaction rate is unsatisfactory. Further, the above-mentioned method is disadvantageous in that the proportion of nitrous acid ester in a reaction mixed gas comprising the nitrous acid ester, carbon monoxide, alcohol and oxygen is higher than an explosion (flammable) limit of the mixed gas, and thus this reaction mixed gas is not preferable in view of the safety of the procedure. Accordingly this method is not satisfactory for practical use.

As mentioned above, the conventional method of producing carbonic acid diester from a nitrous acid ester and carbon monoxide is disadvantageous in that the reaction rate of carbon monoxide with nitrous acid ester is unsatisfactorily low and the selectivity of the resultant carbon acid diester is low, and thus the resultant carbon acid diester must be recovered through complicated purifying procedures. Also, this method is further disadvantageous in that the nitrous acid ester must be employed in a higher content than the explosion limit of the reaction mixed gas, and thus the reaction procedure is dangerous.

Under the above-mentioned circumstances, an object of the present invention is to provide a method of producing a carbonic acid diester by a gas phase reaction procedure under moderate conditions, by which method the carbonic acid diester can be produced with a high selectivity, yield and stability.

In particular, in a practical fixed catalyst bed gas phase process, the activity of the catalyst must be stable for a long time, and the present invention is intended to provide a method suitable for the above-mentioned process.

DISCLOSURE OF THE INVENTION

The inventors of the present invention made an intensive study of a synthetic reaction for producing a carbonic acid diester from a nitrous acid ester, and in particular, a catalyst for producing a carbonic acid diester by a gas phase catalytic reaction of carbon monoxide with a nitrous acid ester, and succeeded in obtaining a solid catalyst by which the carbonic acid diester can be produced under moderate conditions with a very high yield, to thereby complete the present invention.

Namely the method of the present invention produces a carbonic acid diester, and comprises the steps of (A) catalytically reacting carbon monoxide with a nitrous acid ester in a gas phase in the presence of a solid catalyst comprising a solid carrier and a catalytically active solid material carried on the solid carrier and comprising:

(a) at least one member selected from the group consisting of platinum group metals and compounds thereof;
  (b) at least one member selected from the group consisting of iron compounds, copper compounds, bismuth compounds, cobalt compounds, nickel compounds and tin compounds; and
  (c) at least one member selected from the group consisting of vanadium compounds, molybdenum compounds, tungsten compounds, sulfuric acid and phosphoric acid.

BEST MODE OF CARRYING OUT THE INVENTION

The nitrous acid ester usable for the method of the present invention is preferably selected from the group consisting of nitrites of lower aliphatic monohydric alcohols having 1 to 4 carbon atoms, for example, methyl nitrite, ethyl nitrite, n- or iso propyl nitrite, n- or iso butyl nitrite and sec-butyl nitrite; nitrites of cycloaliphatic monohydric alcohols, for example, cyclohexyl nitrite; and nitrites of aralkyl monohydric alcohols, for example, benzyl nitrite and phenylethyl nitrite. Among the above-mentioned nitrous acid esters, the nitrites of aliphatic monohydric alcohols having 1 to 4 carbon atoms are preferable for the present invention, but the most preferable nitrous acid esters for the present invention are methyl nitrite and ethyl nitrite.

The solid catalyst usable for the present invention comprises a solid carrier and a catalytically active material carried on the solid carrier, and comprising (a) a catalyst component (a) consisting of at least one member selected from the group consisting of platinum group metals, for example, palladium, platinum, iridium, ruthenium and rhodium, and compounds of the platinum group metals, preferably platinum group metal compounds;

(b) a catalyst component (b) consisting of at least one member selected from the group consisting of iron compounds, copper compounds, bismuth compounds, cobalt compounds, nickel compounds and tin compounds; and (c) a catalyst component (c) consisting of at least one member selected from the group consisting of vanadium compounds, molybdenum compounds, tungsten compounds, sulfuric acid and phosphoric acid.

Preferably the catalytically active material comprises a catalyst component (a) consisting of a platinum group metal compound, a catalyst component (b) consisting of at least one member selected from iron, copper, bismuth, cobalt, nickel and tin compounds, and a catalyst component (c) consisting of at least one member selected from vanadium compounds, molybdenum compounds, tungsten compounds, sulfuric acid and phosphoric acid.

The above-mentioned platinum group metal compounds preferably include halides, for example, chlorides, bromides, iodides and fluorides, nitrates, sulfates, phosphates, acetates, oxalates and benzoates of the platinum group metals.

More concretely, the platinum group compounds are selected from the group consisting of palladium chloride, palladium bromide, palladium, iodide, palladium fluoride, palladium nitrate, palladium sulfate, palladium phosphate, palladium acetate, palladium oxalate, palladium benzoate, platinum chloride, iridium chloride, ruthenium chloride, ruthenium iodide, rhodium chloride, rhodium bromide, rhodium iodide, rhodium nitrate, rhodium sulfate and rhodium acetate.

Among the above-mentioned, the halides and sulfates of palladium, ruthenium and rhodium are particularly preferable for the present invention, but the most preferable compound for the first catalyst component is palladium chloride.

The above-mentioned metal compounds include halides, for example, chlorides, bromides, iodides, and fluorides, nitrates, sulfates, phosphates, acetates of iron, copper bismuth, cobalt, nickel and tin, and the preferable compounds are halides of the above-mentioned compounds.

The above-mentioned vanadium, molybdenum and tungsten compounds preferably are selected from the group consisting of oxides, metal acids, metal salts of metal acids and ammonium salts of metal acids of vanadium, molybdenum and tungsten. Among the above-mentioned metal compounds, metal oxides, i.e., vanadium oxide, molybdenum oxide and tungsten oxide, and ammonium salts of metal acids, for example, ammonium vanadate, ammonium molybdate and ammonium tungstate are most preferable.

The solid carrier usable for carrying thereon the above-mentioned metal compounds preferably comprises at least one member selected from the group consisting of diatomaceous earth, activated carbon, silicon carbide, titania, alumina and silica-alumina, but the most preferable material for the solid carrier is activated carbon.

The catalytically active solid material can be carried on the solid carrier by a conventional application method, for example, an impregnating method (an immersion and absorption method), a mix-kneading method, a precipitation method, an evaporation-drying method, or a co-precipitation method. Preferably, in the preparation of the solid catalyst of the present invention, the impregnating method and the evaporation-drying method are utilized. In the preparation of the solid catalyst, the above-mentioned components may be carried at one time or carried successively in steps.

In the solid catalyst of the present invention, the catalyst component (a) is preferably present in an amount, in terms of the platinum group metal as used, of 0.1% to 10% by weight, more preferably 0.5% to 2% by weight, based on the weight of the solid carrier.

Also, as the catalyst component (b), the iron, copper, bismuth, cobalt, nickel or tin compound preferably is carried in an amount, in terms of the metal as used, of 0.1 to 50 gram atom equivalents, more preferably 1 to 10 gram atom equivalents, per gram atom equivalent of the platinum group metal contained therein, on the carrier.

In the method of the present invention, as the catalyst component (c), the vanadium, molybdenum or tungsten compound preferably is carried in an amount, in terms of the metal as used, of 0.1 to 20 gram atom equivalents, more preferably 0.5 to 5 gram atom equivalents, per gram atom equivalent of the platinum group metal, on the solid carrier.

In the method of the present invention, as the catalyst component (c), sulfuric acid or phosphoric acid preferably is carried in an amount, in terms of the metal as used, of 0.1 to 20 gram atom equivalent, more preferably 0.5 to 10 gram atom equivalent, per gram atom equivalent of the platinum group metal, on the carrier.

In the method of the present invention, when the catalyst components (b) and (c) are carried in the above-mentioned amounts on the carrier, the resultant solid catalyst exhibits a lower deactivation rate and a significantly longer catalyst durability than those of a catalyst obtained when the catalyst component (b) and/or (c) is not employed.

Also, in the present invention, the above-mentioned solid catalyst is in the form of powdery particles, i.e., fine particles, grains or other shaped articles. There is no limitation of the size of the solid catalyst.

Preferably, the solid catalyst in the form of fine particles has a size of from 20 to 100 $\mu$m.

Also, the solid catalyst in the form of grains preferably has a mesh size of from 4 to 200.

Further, the solid catalyst in the form of shaped articles preferably has a size of several mm.

When the specific solid catalyst of the present invention is employed, the catalytic reaction of a nitrous acid ester with carbon monoxide can be effectively conducted even under moderate conditions; this is one of the advantages of the method of the present invention.

For example, the catalytic reaction in the method of the present invention can be effected at a temperature of from 0° C. to 200° C., preferably from 50° C. to 140° C., under the ambient atmospheric pressure. The catalytic reaction can be carried out in a pressurized system, for example, under a pressure of 1 to 20 kg/cm²G and at a temperature of 50° C. to 140° C.

In the method of the present invention, the nitrous acid ester can be easily prepared, for example, by decomposing sodium nitrite in an aqueous solution in the presence of nitric acid or sulfuric acid to generate a mixed gas of nitrogen monoxide (NO) and nitrogen dioxide ($NO_2$), oxidizing a portion of the nitrogen monoxide in the mixed gas with molecular oxygen to convert same to $NO_2$ and to provide a NOx gas having a molar ratio of nitrogen monoxide to nitrogen dioxide, $NO/NO_2$ of 1/1, and bringing the NOx gas into contact with an alcohol.

In view of the preparation step of the nitrous acid ester, the catalytic reaction of the nitrous acid ester with carbon monoxide is preferably carried out under a slightly higher pressure than the ambient atmospheric pressure, for example, 2 to 3 kg/cm²G.

In the method of the present invention, the catalytic reaction step of the nitrous acid ester with carbon monoxide is carried out in a gas phase. This reaction can be carried out in a batch system or a continuous reaction system. The continuous reaction system is advantageous for an industrial production of the carbonic acid diester. In any reaction system, the solid catalyst of the present invention may be placed in a fixed catalyst bed or a fluidized catalyst bed of a reactor.

In the method of the present invention, the starting gas comprising carbon dioxide and a nitrous acid ester is preferably diluted with an inert gas, for example, nitrogen gas and fed into the above-mentioned reaction system.

The reaction system need not have a specific composition, but from the viewpoint of safety, the content of the nitrous acid ester in the inert gas atmosphere is preferably 20% by volume or less, more preferably, 5 to 20% by volume. Also, from the viewpoint of economy, the content of carbondioxide is from 5% to 20% by volume. Namely, in an industrial production process, the carbon monoxide and nitrous acid ester gases are preferably recycled, and after the catalytic reaction step is completed, a portion of the recycled gas is purged to the outside of the reaction system.

Usually, carbon monoxide is consumed at a conversion rate of 20% to 30% by volume in a one path reaction and therefore, a content of carbon monoxide of more than 20% by volume does not bring any advantage but results in a lower efficiency. Also, a content of carbon monoxide of less than 5% by volume brings an unsatisfactory productivity. Nevertheless, if this low economic efficiency is ignored, the carbon monoxide can be employed in a content of 80% by volume or less. In this case, the carbon monoxide serves as a dilute gas, in place of the inert gas, for the nitrous acid ester, and the resultant diluted gas can be fed to the reaction system.

In the method of the present invention, the feed gas preferably contains carbon monoxide in a molar ratio to a nitrous acid ester of 0.1/1 to 10/1, more preferably 0.25/1 to 1/1.

Also, in the method of the present invention, the feed gas containing the nitrous acid ester and carbon monoxide is preferably fed during the catalytic reaction step at a space velocity of 500 to 20,000 hr$^{-1}$, more preferably 2,000 to 15,000 hr$^{-1}$.

In the method of the present invention, the reaction of the nitrous acid ester with carbon monoxide produces nitrogen monoxide (NO) as a by-product. Therefore, the nitrogen monoxide gas is preferably recovered from the resultant reaction product gas discharged from the reaction system and then fed to a reaction of oxygen with an alcohol corresponding to the nitrous acid ester, to thus re-produce a nitrous acid ester. Namely, the NO gas is recycled and reused.

The resultant reaction mixture of the catalytic reaction step contains, in addition to the aimed carbonic acid diester, oxalic acid diester as a by-product, non-reacted nitrous acid ester and carbon monoxide, carbon dioxide, and an inert gas.

To separate and refine the aimed carbonic acid diester from the reaction mixture gas, for example, the resultant reaction mixture is cooled to condense same, a portion of a non-condensed gas comprising carbon monoxide, nitrous acid ester, nitrogen monoxide, carbon dioxide and inert dilute gas is purged, and the purged non-condensed gas is returned to the reaction system. Also, the condensed liquid obtained from the cooling procedure is used to recover the aimed carbonic acid diester by a customary refining process, for example, distillation.

As mentioned above, the nitrous acid ester usable as a starting material for the method of the present invention is prepared by a reaction of an alcohol with nitrogen oxides, optionally in the presence of molecular oxygen. Therefore, the resultant product contains, in addition to the nitrous acid ester, non-reacted alcohol, nitrogen oxides (mainly nitrogen monoxide), and sometimes, a small amount of water and/or oxygen. In the method of the present invention, the above-mentioned nitrous acid ester-containing gas can be used as a nitrous acid ester-supply source, and even in this case, a satisfactory result is obtained.

EXAMPLES

The present invention will be further explained by the following specific examples, which are merely representative and in no way restrict the scope of the present invention.

In each of the examples and comparative examples, the space time yield (STY) in g/l·hr of the resultant product was calculated in accordance with the following equation:

$$Y = a/(b \times \theta)$$

wherein Y represents a space time yield in g/l·hr of the product, $\theta$ represents a reaction time in hours of carbon monoxide with a nitrous acid ester, a represents a weight in grams of the resultant carbonic acid diester during the reaction time $\theta$, and b represents a volume in liters of a solid catalyst present in the reaction tube.

Also, in each of the examples, and comparative examples, the catalytic activity reduction coefficient of a catalyst was calculated in accordance with the following equations:

$$Y_t = Y_0 \cdot exp(-kt)$$

$$Da = 100 \times k$$

wherein Da represents a catalytic activity reduction coefficient in hr$^{-1}$ of the catalyst under predetermined reaction conditions, Yo represents a space time yield in g/l·hr of the product in an initial stage of the reaction procedure, i.e., 2 hours after the start of the reaction, Yt represents a space time yield in g/l·hr of the product at t hours after the start of the reaction, and k is a constant obtained from the equation Yt=Yo·exp(−kt).

Example 1

Preparation of Catalyst

A Pd Cu and Mo—containing aqueous solution was prepared by heat-dissolving 0.33 g of palladium chloride (PdCl$_2$), 0.65 g of cupric chloride (CuCl$_2$·2H$_2$O) and 0.80 g of ammonium molybdate [(NH$_4$)$_6$Mo$_7$O$_{24}$·4H$_2$O] in 70 ml of an aqueous solution of 28% by weight of ammonia at a temperature of 80° C. to 90° C.

Separately, particulate activated carbon (C) having a size of 0.5 to 0.7 mm was immersed and dispersed in an aqueous solution of 28% by weight of ammonia, then the above-mentioned Pd, Cu and Mo—containing solution was mixed with the activated carbon dispersion. The resultant mixture was left to stand for one hour.

The mixture was then subjected to water evaporation at a temperature of 80° C. under a reduced pressure, and dried in a nitrogen gas atmosphere at a temperature of 200° C. to provide a solid catalyst.

The resultant solid catalyst has an empirical composition of PdCl$_2$—CuCl$_2$—(NH$_4$)$_6$Mo$_7$O$_{24}$/C (activated carbon).

The Pd compound in the catalyst was present in an amount in terms of metallic palladium of 1% based on the weight of the solid carrier consisting of the activated carbon. The content ratio Pd:Cu:Mo was 1:2:2.1 (atomic ratio).

Production of a Carbonic Acid Diester

The above-mentioned solid catalyst in an amount of 1.5 ml was placed in a gas phase reaction tube having an inside diameter of 20 mm and equipped with an outside jacket. The reaction tube filled by the solid catalyst was fixed vertically and a heating medium was made to flow through the outside jacket to maintain the inside temperature of the reaction tube at a level of 120° C.

A mixed gas containing methyl nitrite prepared from nitrogen monoxide, oxygen and methyl alcohol with carbon monoxide, i.e., consisting of 8% by volume of methyl nitrite, 8% by volume of carbon monoxide, 3% by volume of nitrogen monoxide, 10% by volume of methyl alcohol and 71% by volume of nitrogen, was fed into the reaction tube through a top end thereof at a space velocity (GHSV) of 15,000 hr$^{-1}$ under the ambient atmospheric pressure, to cause the carbon monoxide to react with the methyl nitrite.

Then, the resultant reaction product passed through the reaction tube was made to flow through methyl alcohol cooled with ice, and the resultant reaction product collected.

The collected reaction product was subjected to a gas chromatography, and it was confirmed that, at 2 hours after the start of the reaction procedure, the space time yield (STY) of dimethyl carbonate was 402 g/l·hr, and at 9 hours after the start of the reaction procedure, the STY of dimethyl carbonate was 381 g/l·hr, and thus the solid catalyst exhibited a catalytic activity reduction coefficient Da of 1.1 hr$^{-1}$.

Comparative Example 1

Preparation of a Catalyst

First, 0.33 g of palladium chloride (PdCl$_2$) and 0.64 g of cupric chloride (CuCl$_2$·2H$_2$O) were heat-dissolved in 100 ml of a 5 N hydrochloric acid, and then the same particulate activated carbon as used in Example 1 was immersed in an amount of 20 g in the above-mentioned solution, filtered, washed with water, and then dried at 80° C. under a reduced pressure to remove water, and further dried at 200° C. in a nitrogen gas atmosphere, to provide a solid catalyst.

The empirical composition of the resultant solid catalyst was PdCl$_2$—CuCl$_2$/C (activated carbon). In this solid catalyst, the content of the Pd compound in terms of palladium was 1% based on the weight of the activated carbon carrier and the atom equivalent ratio of the metals (Pd and Cu) was Pd:Cu=1:2.

Production of Dimethyl Carbonate

The same dimethyl carbonate production procedures as in Example 1 were carried out except that the above-mentioned catalyst was used in place of the catalyst of Example 1.

The collected liquid was subjected to a gas chromatographic analysis, and it was confirmed that the STY of dimethyl carbonate was 455 g/l·hr at 2 hours after the start of the reaction procedure and 374 g/l at 6 hours after the start of the reaction procedure, and the catalytic activity reduction coefficient of the catalyst Da was 5.0 hr$^{-1}$.

Examples 2 to 10

In each of Example 2 to 10, the same procedures as in Example 1 were carried out with the following exceptions.

Preparation of Catalyst

A solid catalyst having a catalyst composition and metal atomic ratio of catalyst components as shown in Table 1 were prepared.

Preparation of Dimethyl Carbonate

The above-mentioned catalyst was used. The results are shown in Table 1.

Comparative Examples 2 and 3

In each of Comparative Examples 2 and 3, the same procedures as in Example 1 were carried out, with the following exceptions.

Preparation of Catalyst

A solid catalyst having the catalyst composition and the metal atomic ratio of the catalyst components as shown in Table 1 was prepared.

Preparation of Dimethyl Carbonate

The above-mentioned catalyst was used. The results are shown in Table 1.

TABLE 1

| Example No. | Empirical composition of catalyst/Carrier | Gram atom equivalent ratio of metals in catalyst | Initial STY(*) Yo (g/l · hr) | Catalytic activity reduction coefficient Da (hr$^{-1}$) |
|---|---|---|---|---|
| Example | | | | |
| 2 | PdCl$_2$—CuCl$_2$—NH$_4$VO$_3$/C | Pd/Cu/V = 1/2/1 | 430 | 1.0 |
| 3 | PdCl$_2$—CuSO$_4$—(NH$_4$)$_{10}$HW$_{12}$O$_{46}$/C | Pd/Cu/W = 1/2/1 | 375 | 0.8 |
| 4 | PdCl$_2$—FeCl$_3$—VOSO$_4$/TiO$_2$ | Pd/Fe/V = 1/1/1 | 383 | 1.2 |
| 5 | PdCl$_2$—BiCl$_3$—(NH$_4$)$_6$MoO$_{24}$/C | Pd/Bi/Mo = 1/5/3 | 352 | 0.4 |
| 6 | PdSO$_4$—CoCl$_2$—NH$_4$VO$_3$/Diatomaceous | Pd/Co/V = 1/2/1 | 325 | 0.5 |
| 7 | RhCl$_3$—NiCl$_2$—NH$_4$VO$_3$/C | Rh/Ni/V = 1/2/1 | 281 | 0.4 |
| 8 | RuCl$_4$—SnCl$_4$—NH$_4$VO$_3$/C | Ru/Sn/V = 1/2/1 | 253 | 1.8 |
| 9 | PdCl$_2$—CuCl$_2$—NH$_4$VO$_3$/C | Pd/Cu/V = 1/2/0.5 | 395 | 1.5 |
| 10 | PdCl$_2$—CuCl$_2$ + FeCl$_3$—NH$_4$VO$_3$/C | Pd/Cu/Fe/V = 1/1/1/2 | 417 | 0.5 |
| Comparative Example | | | | |
| 2 | PdCl$_2$—CuCl$_2$—NH$_4$VO$_3$/C | Pd/Cu/V = 1/2/0.01 | 410 | 4.5 |
| 3 | PdCl$_2$—FeCl$_3$—NH$_4$VO$_3$/C | Pd/Cu/V = 1/2/25 | 85 | 0.5 |

Note:
(*) ... Space time yield in g/l · hr of dimethyl carbonate 2 hours after start of reaction procedure

Example 11 (Preparation of dimethyl carbonate)

The same procedures as in Example 1 were carried out except that the reaction temperature was changed from 120° C. to 100° C., to prepare dimethyl carbonate.

The initial STY(Yo) of dimethyl carbonate at 2 hours after the start of the reaction procedure was 280 g/l·hr and the catalytic activity reduction coefficient Da was 0.1 hr$^{-1}$.

Example 12 (Preparation of dimethyl carbonate)

The same procedures as in Example 1 were carried out except that the reaction temperature was changed from 120° C. to 140° C., to prepare dimethyl carbonate.

The initial STY(Yo) of dimethyl carbonate at 2 hours after the start of the reaction procedure was 720 g/l·hr and the catalytic activity reduction coefficient Da was 2.0 hr$^{-1}$.

Example 13 (Preparation of diethyl carbonate)

The same procedures as in Example 1 were carried out except that, in the mixed gas fed to the reaction tube through the top thereof, the methyl nitrite was replaced by ethyl nitrite and methyl alcohol was replaced by ethyl alcohol, to prepare diethyl carbonate.

The initial STY(Yo) of diethyl carbonate at 2 hours after the start of the reaction procedure was 520 g/l·hr and the catalytic activity reduction coefficient Da was 1.2 hr$^{-1}$.

Example 14 (Preparation of dimethyl carbonate)

The same procedures as in Example 1 were carried out except that the same solid catalyst as prepared in Example 1 was charged in an amount of 8.5 ml in the reaction tube, and the mixed gas consisting of 9% by volume of methyl nitrite, 9% by volume of carbon monoxide, 4% by weight of nitrogen monoxide, 3% by volume of methyl alcohol and 75% by volume of nitrogen was fed at a space velocity (GHSV) of 2,500 hr$^{-1}$ and reacted under a pressure of 2.0 kg/cm$^2$, to prepare dimethyl carbonate.

The STY of dimethyl carbonate was 260 g/l·hr at 2 hours after the start of the reaction procedure and 260 g/l·hr even at 22 hours after the start of the reaction procedure, and thus no reduction in the catalytic activity occurred.

Example 15

Preparation of Catalyst

A mixture was prepared by dissolving 0.67 g of palladium chloride (PdCl$_2$) and 1.28 g of cupric chloride (CuCl$_2$·2H$_2$O) in 150 ml of an 1 N sulfuric acid (39.8 gram molecule equivalent of sulfuric acid per gram equivalent of metallic palladium). Particulate activated carbon in an amount of 40 g was immersed in the above-mentioned mixture and stirred for one hour. Thereafter, water in the mixture was removed under a reduced pressure by using a rotary evaporator, and the resultant product was further dried at 200° C. to provide a solid catalyst.

The empirical composition of the resultant catalyst was PdCl$_2$—CuCl$_2$/C, the content of the metal compound, in terms of metallic palladium, in the catalyst was 1%, based on the weight of the carrier, and the ratio Pd:Cu was 1:2 (atomic ratio).

Preparation of dimethyl carbonate

An amount of 1.5 ml of the above-mentioned catalyst was placed in a gas phase reaction tube having an inside diameter of 20 mm and equipped with an outside jacket. The reaction tube was fixed vertically and a heating medium was made to flow through the outside jacket to control the inside temperature of the reaction tube to a level of 120° C.

A mixed gas containing methyl nitrite prepared from nitrogen monoxide, oxygen and methyl alcohol and carbon monoxide, i.e., consisting of 8% by volume of methyl nitrite, 8% by volume of carbon monoxide, 3% by volume of nitrogen monoxide, 10% by volume of methyl alcohol and 71% by volume of nitrogen, was fed into the reaction tube through the top portion thereof at a space velocity (GHSV) of 15,000 hr$^{-1}$, to react carbon monoxide with the nitrous acid ester under the ambient atmospheric pressure.

Then, the reaction product passed through the reaction tube was made to flow through methyl alcohol cooled with ice, and was collected.

The collected reaction product was subjected to a gas chromatography, and as a result, it was confirmed that the STY of dimethyl carbonate was 424 g/l·hr at 2 hours after the start of the reaction procedure and 418 g/l·hr at 7 hours after the start of the reaction procedure, and thus the catalytic activity reduction coefficient Da of the solid catalyst was 0.2 hr$^{-1}$.

Comparative Example 4

Preparation of Catalyst

A solution was prepared by dissolving 0.67 g of palladium chloride (PdCl$_2$) and 1.28 g of cupric chloride (CuCl$_2$·2H$_2$) in 150 ml of an 1 N hydrochloric acid, and 40 g of particulate activated carbon were immersed in the resultant solution. The mixture was stirred for one hour, water in the mixture was removed under a reduced pressure by using a rotary evaporator, and the resultant product was dried at 200° C. in a nitrogen gas atmosphere to provide a catalyst.

The resultant catalyst had an empirical composition of PdCl$_2$—CuCl$_2$/C, the amount of the metal compounds, in terms of metallic palladium, in the catalyst was 1%, based on the weight of the carrier, and the atomic ratio Pd:Cu was 1:2.

Preparation of Dimethyl Carbonate

The above-mentioned catalyst was used.
The results are shown in Table 2.

Comparative Examples 5 to 8

In Comparative Examples 5 to 8, the same procedures were used as in Examples 3 to 6, respectively, with the following exceptions.

Preparation of Catalyst

A solid catalyst was prepared by using an 1 N hydrochloric acid in phase of the 1 N sulfuric acid. In the resultant catalyst, the amount of the palladium group metal compound in terms of the palladium group metal was 1.0%, based on the weight of the carrier.

Preparation of Dimethyl Carbonate

In each comparative example, the above-mentioned catalyst was employed, and the results are shown in Table 2.

TABLE 2

| | | | Item | | | |
|---|---|---|---|---|---|---|
| Example No. | Empirical composition of catalyst/Carrier | Gram atom equivalent ratio of metals in catalyst | Acid Type | Acid Amount | Initial STY(*) Yo (g/l · hr) | Catalytic activity reduction coefficient Da (hr$^{-1}$) |
| Example | | | | | | |
| 16 | PdCl$_2$—CuCl$_2$/C | Pd/Cu = 1/2 | 1N H$_3$PO$_4$ | 150 ml | 200 | 1.0 |
| 17 | PdCl$_2$—CuCl$_2$/γ-Al$_2$O$_3$ | Pd/Cu = 1/2 | 1N H$_2$SO$_4$ | 150 ml | 350 | 0.4 |
| 18 | PdCl$_2$—FeCl$_3$/C | Pd/Fe = 1/1 | 1N H$_2$SO$_4$ | 150 ml | 240 | 0.9 |
| 19 | RhCl$_3$—CuCl$_2$/C | Rh/Cu = 1/2 | 1N H$_2$SO$_4$ | 150 ml | 110 | 1.1 |
| 20 | PdCl$_2$—BiCl$_3$/C | Pd/Bi = 1/5 | 1N H$_2$SO$_4$ | 150 ml | 265 | 0.9 |
| Comparative Example | | | | | | |
| 5 | PdCl$_2$—CuCl$_2$/γ-Al$_2$O$_3$ | Pd/Cu = 1/2 | 1N HCl | 150 ml | 370 | 9.3 |
| 6 | PdCl$_2$—FeCl$_3$/C | Pd/Fe = 1/1 | 1N HCl | 150 ml | 260 | 9.5 |
| 7 | RhCl$_3$—CuCl$_2$/C | Rh/Cu = 1/2 | 1N HCl | 150 ml | 120 | 8.6 |
| 8 | PdCl$_2$—BiCl$_3$/C | Pd/Bi = 1/5 | 1N HCl | 150 ml | 280 | 7.2 |

Note:
(*) . . . Space time yield in g/l · hr of dimethyl carbonate 2 hours after start of reaction procedure The same procedurers as in Example 1 were carried out, except that the above-mentioned catalyst was used, to prepare dimethyl carbonate.

The resultant reaction product was subjected to a gas chromatography, and as a result, the STY of dimethyl carbonate was 590 g/l·hr at 2 hours after the start of the reaction procedure and 426 g/l·hr at 6 hours after the start of the reaction procedure, and thus the catalytic activity reduction coefficient Da of the catalyst was 5.4 hr$^{-1}$.

Examples 16 to 20

In each of Examples 16 to 20, the same procedures as in Example 15 were carried out, with the following exceptions.

Preparation of Catalyst

A solid catalyst having the catalyst composition and the metal atomic ratio of the catalyst components as indicated in Table 2 was prepared by using the acid as shown in Table 1.

The amount of the palladium group metal compound in the solid catalyst was 1% by weight, in terms of palladium group metal, based on the weight of the carrier.

Example 21 (Preparation of Dimethyl Carbonate)

The same procedures as in Example 15 were carried out, except that the inside temperature of the catalyst layer was changed from 120° C. to 100° C., to produce dimethyl carbonate.

The STY of dimethyl carbonate at 2 hours after the start of the reaction procedure was 273 g/l·hr, and the catalytic activity reduction efficiency Da was 0.1 hr$^{-1}$.

Example 22 (Preparation of Dimethyl Carbonate)

The same procedures as in Example 15 were carried out, except that the inside temperature of the catalyst layer was changed from 120° C. to 140° C., to prepare dimethyl carbonate.

The STY of dimethyl carbonate at 2 hours after the start of the reaction procedure was 610 g/l·hr, and the catalytic activity reduction coefficient Da was 3.0 hr$^{-1}$.

Example 23 (Preparation of Dimethyl Carbonate)

The same procedures as in Example 15 were carried out, except that in the mixed gas fed to the reaction tube through the top portion thereof, the methyl nitrite was replaced by ethyl nitrite, and methyl alcohol was replaced by ethyl alcohol, to provide diethyl carbonate.

The STY of diethyl carbonate at 2 hours after the start of the reaction procedure was 410 g/l·hr, and the catalytic activity reduction coefficient Da was 0.3 hr$^{-1}$.

Example 24 (Preparation of Dimethyl Carbonate)

The same procedures as in Example 15 were carried out, except that the same solid catalyst as prepared in Example 15 was charged in an amount of 8.5 ml in the reaction tube, and the mixed gas consisting of 9% by volume of methyl nitrite, 9% by volume of carbon monoxide, 4% by weight of nitrogen monoxide, 3% by volume of methyl alcohol and 75% by volume of nitrogen was fed at a space velocity (GHSV) of 2,500 hr$^{-1}$ and reacted under a pressure of 2.0 kg/cm$^2$, to prepare dimethyl carbonate.

The STY of dimethyl carbonate was 380 g/l·hr at 2 hours after the start of the reaction procedure and 290 g/l·hr even at 30 hours after the start of the reaction procedure, and thus no reduction in the catalytic activity occurred.

CAPABILITY OF EXPLOITATION IN INDUSTRY

The conventional method of preparing carbonic acid diester by a gas phase catalytic reaction of carbon monoxide with a nitrous acid ester does not provide a fully satisfactory reaction rate, and is disadvantageous in that the selectivity of carbonic acid diester is low, the separation-refining procedure of carbonic acid diester from the resultant reaction product is complicated, and the concentration range of the nitrous acid ester contained in a reaction system exceeds an explosion limit thereof, i.e., this reaction procedure is dangerous.

In comparison, the method of the present invention makes it possible to prepare a carbonic acid diester with a high selectivity, a high yield and a high safety, without the danger arising from reacting in a gas phase carbon monoxide with a nitrous acid ester in the presence of a solid catalyst, in which the above-mentioned specific catalyst components (a), (b) and (c) are carried on a carrier under moderate conditions.

Also, compared with the conventional liquid phase method, the method of the present invention is carried out in a gas phase, and thus a procedure for removing the catalyst from the reaction product is not necessary and no elution of metallic components of the catalyst into the reaction product occurs. Therefore, the refining of the carbonic acid diester from the reaction product is made easy.

Accordingly, the method of the present invention of producing a carbonic acid diester is extremely useful for an industrial scale production.

We claim:

1. A method of producing a carbonic acid diester, characterized by catalytically reacting carbon monoxide with a nitrous acid ester in a gas phase in the presence of a solid catalyst composed of a solid carrier and a catalytic solid material carried on the carrier, and comprising:
   (a) at least one member selected from the group consisting of platinum group metals and compounds thereof;
   (b) at least one member selected from the group consisting of iron compounds, copper compounds, bismuth compounds, cobalt compounds, nickel compounds and tin compounds; and
   (c) at least one member selected from the group consisting of vanadium compounds, molybdenum compounds and tungsten compounds, sulfuric acid and phosphoric acid.

2. The method as claimed in claim 1, wherein the nitrous acid ester is selected from the group consisting of nitrites of lower aliphatic monohydric alcohols having 1 to 4 carbon atoms, nitrites of cycloaliphatic alcohols and nitrites of aralkyl alcohols.

3. The method as claimed in claim 1, wherein the platinum group metal compound is selected from the group consisting of halides, nitrates, sulfates, phosphates, acetates, oxalates, and benzoates of the palladium group metals.

4. The method as claimed in claim 1, wherein the compounds of iron, copper, bismuth, cobalt, nickel and tin are selected from halides, nitrates, sulfates, phosphates and acetates of the above-mentioned metals.

5. The method as claimed in claim 1, wherein the compounds of vanadium molybdem and tungsten are selected from oxides, metal acids, metal acid salts, and metal acid ammonium salts of the above-mentioned metals.

6. The method as claimed in claim 1, wherein the solid carrier is selected from the group consisting of diatomaceous earth, activated carbon, silicon carbide, titania, alumina and silica-alumina.

7. The method as claimed in claim 1, wherein the catalyst components (a), (b) and (c) are carried on the carrier by one of an impregnation method, mix-kneading method, precipitation method, evaporation-drying solidification method, and co-precipitation method.

8. The method as claimed in claim 1, wherein the catalyst component (a) is present in an amount of from 0.1 to 10% by weight in terms of the corresponding metal, based on the weight of the solid carrier.

9. The method as claimed in claim 1, wherein the catalyst component (b) is present in an amount in terms of the metal of 0.1 to 50 gram atom equivalents per gram atom equivalent of the catalyst component (a) in terms of the platinum group metal.

10. The method as claimed in claim 1, wherein the catalyst component (c) consists of at least one member selected from the vanadium compounds, molybdenum compounds and tungsten compounds, and the amount of the catalyst component (c) carried on the carrier is 0.1 to 20 gram atom equivalents in terms of the metal, per gram atom equivalent of the catalyst component (a) in terms of the platinum group metal.

11. The method as claimed in claim 1, wherein the catalyst component (c) consists of at least one member selected from sulfuric acid and phosphoric acid, and the amount of the catalyst component (c) carried on the carrier is 1 to 100 gram atom equivalents per gram atom equivalent of the catalyst component (a), in terms of the platinum group metal.

12. The method as claimed in claim 1, wherein the solid catalyst is in the form of powdery particles.

13. The method as claimed in claim 1, wherein the catalytic reaction of carbon monoxide with the nitrous acid ester is carried out at a temperature of 0° to 200° C. under a pressure of from 0 to 20 kg/cm$^2$G.

14. The method as claimed is claim 1, wherein the nitrous acid ester is synthesized by a catalytic reaction of a mixed gas of nitrogen monoxide and nitrogen dioxide with an alcohol.

15. The method as claimed in claim 1, the catalytic reaction of the carbon monoxide with the nitrous acid ester is carried out in an inert gas atmosphere.

16. The method as claimed in claim 14 wherein, in the inert gas atmosphere, the concentration of the carbon monoxide and nitrous acid ester respectively is 20% by weight or less.

17. The method as claimed in claim 1, wherein carbon monoxide subjected to the gas phase catalytic reaction is in an amount of 0.1 to 10 moles per mole of the nitrous acid ester.

18. The method as claimed in claim 1, wherein a gas containing the carbon monoxide and the nitrous acid ester is fed at a space velocity of 500 to 20,000 $hr^{-1}$ into the gas phase catalytic reaction system.

* * * * *

UNITED STATES PATENT AND TRADEMARK OFFICE
CERTIFICATE OF CORRECTION

PATENT NO. : 5,292,916

DATED : March 8, 1994

INVENTOR(S) : Tokuo MATSUZAKI et al.

It is certified that error appears in the above-identified patent and that said Letters Patent is hereby corrected as shown below:

Claim 5, column 14, line 18, delete "vanadium molybdem" and insert --vanadium, molybdenum--.

Signed and Sealed this

Second Day of August, 1994

Attest:

BRUCE LEHMAN

Attesting Officer     Commissioner of Patents and Trademarks